Figure 1:
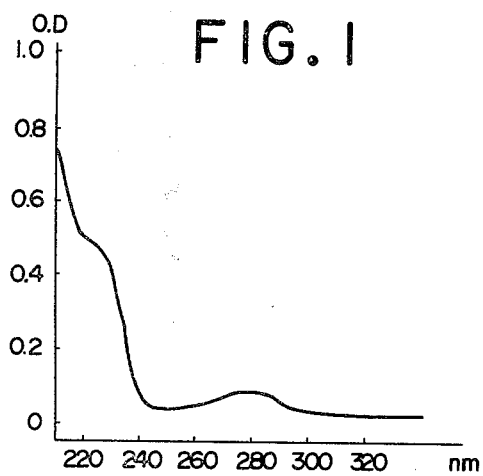

United States Patent [19]
Otani et al.

[11] 4,212,858
[45] Jul. 15, 1980

[54] ANTIBIOTIC ACULEACIN-Aα, -Aγ, -Dα AND -Dγ AND METHODS FOR THEIR PRODUCTION

[75] Inventors: Masaru Otani; Shuzo Satoi; Masaki Takada, all of Shizuoka, Japan

[73] Assignee: Toyo Jozo Kabushiki Kaisha, Shizuoka, Japan

[21] Appl. No.: 897,919

[22] Filed: Apr. 19, 1978

[30] Foreign Application Priority Data

| Apr. 19, 1977 | [JP] | Japan | 52-46078 |
| Apr. 19, 1977 | [JP] | Japan | 52-46079 |
| Apr. 19, 1977 | [JP] | Japan | 52-46080 |
| Apr. 19, 1977 | [JP] | Japan | 52-46081 |

[51] Int. Cl.$^2$ .................. A61K 35/70; C12P 1/02
[52] U.S. Cl. .................. 424/118; 424/119; 435/171; 435/913; 435/68
[58] Field of Search .................. 195/81; 424/118, 119; 435/68, 171

[56] References Cited

U.S. PATENT DOCUMENTS 3,978,210   8/1976   Mizuno et al. .................. 195/81

Primary Examiner—Alvin E. Tanenholtz
Attorney, Agent, or Firm—Young & Thompson

[57] ABSTRACT

Antibiotics aculeacin-Aα, -Aγ, -Dα and -Dγ are active against yeasts and fungi. They are produced by culturing the microorganism *Aspergillus aculeatus* NRRL 11270 in a nutrient medium containing assimilable carbon and nitrogen sources.

6 Claims, 12 Drawing Figures

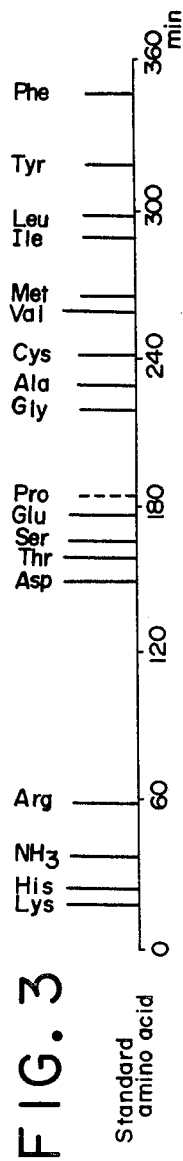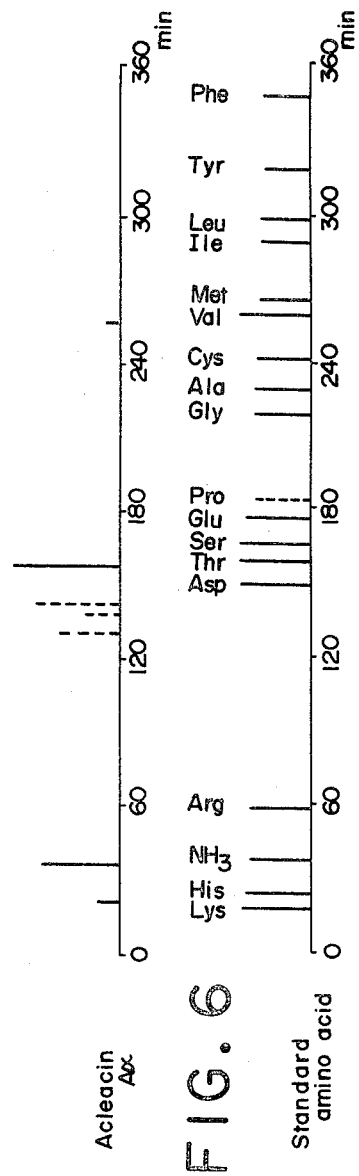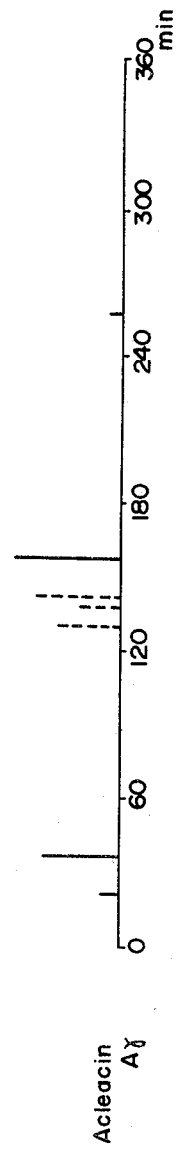
FIG. 3  FIG. 6

ANTIBIOTIC ACULEACIN-Aα, -Aγ, -Dα AND -Dγ AND METHODS FOR THEIR PRODUCTION

This invention relates to novel antibiotics aculeacin-Aα, -Aγ, -Dα and -Dγ and to methods for their production.

We have found that a fungus belonging to genus Aspergillus, strain No. M 4845 produced novel antibiotics active against yeasts such as *Candida albicans* and fungi such as dermatophytes and plant pathogenic fungi at low concentrations, and designated as aculeacin-Aα, -Aγ, -Dα and -Dγ.

The said Aspergillus strain M 4845 has the following taxonomic properties.

A. Macroscopic Observation

1. Czapeck agar medium:
Growth: rapid, diameter 55–65 mm. at 26° C., in 10 days.
Surface of colony: plane and thin; white at an early stage of culture; fawn (hue 41g) dependent on the degree of formation of conidia. Formation of conidia is abundant.
Periphery of colony: slight arachnoid.
Reverse of colony: colorless–pale yellow (hue 1ca).
No formation of diffusible pigment and exudate.
Growth at 37° C.: slow; 14–17 mm. in 10 days.

2. Malt extract agar medium:
Growth: rapid, diameter 60–70 mm. at 26° C., in 10 days.
Surface of colony: plane and thin, white at an early stage of culture; beaver (hue 41i) dependent on the degree of formation of conidia.
Conidia: large amount of formation.
Periphery of colony: smooth or almost smooth.
Reverse of colony: light yellow (hue 1½ca).
No formation of diffusible pigment and exudate.
Growth at 37° C.: slow; 10–12 mm. in 10 days.

3. Potato-glucose agar medium:
Growth rate and condition: similar to those on malt extract agar medium, except clearly arachnoid periphery of colony.
Indication of color is based on the indication in "Color Harmony Manual", Ed. 1958, published by Container Corporation of America.

B. Microscopic Observation

Conidial head is globose at early stage, then radially segmented into several columns. Length of conidiophore is 400–1500μ. Width is 8–13μ, colorless light yellowish brown and wall is smooth and slightly thick. Thickness is about 1.5–2.0μ. Vesicle is light brown and globose or nearly globose; diameter 30–75μ, mainly 40–60μ. Sterigma appears uniseriate with size of 6–8×3–4μ closely in line. Conidium is generally globose or elliptical, showing variety of form, and size is 3.5–5.0×3.0–3.5μ, light yellowish brown colored and wall is rough.

C. Growth Conditions

Growth temperature: 13°–40° C. Growth pH: 2–9.
Optimum growth temperature and pH: 29°–31° C., pH 3–5.

According to the taxonomical studies hereinbefore, this strain belongs to *Aspergillus niger* group [refer to Japan. J. Agrical. Chem., 27, 806–809 (1953), and the genus Aspergillus 328–331 (1965)] having black brown conidia. Further, this group is differentiated in two groups according to uniseriate orbiseriate sterigma. This strain belongs to the uniseriated group. At present, fungi having uniseriated sterigma have been known as *Aspergillus japonicus* and *Aspergillus aculeatus*, and since in the *Aspergillus japonicus*, conidium is globose or subglobose of 3–3.5 μ, and vesicle is 15–45μ, mainly 20–35μ, and in the *Aspergillus aculeatus*, conidium is subglobose or elliptical of 4.5–5×3–3.5μ, and vesicle is 35–100μ, mainly 60–80μ, therefore this strain resembles *Aspergillus aculeatus* in taxonomy. Furthermore, the strain *Aspergillus aculeatus* ATCC 1034 obtained from American Type Culture Collection and this strain resemble each other upon comparison, whereby this strain is referred to as *Aspergillus aculeatus* M 4845. This strain has been deposited in the Institute for Industrial Fermentation and Technology, Agency of Industrial Science and Technology, Japan, and assigned the permanent deposit number FERM-P No. 4023. Also this strain is deposited in the United States Department of Agriculture, Agricultural Research Service, Northern Utilization Research and Development Division, and added to its permanent collection as deposit number NRRL 11270.

An object of the present invention is to provide novel antibiotics aculeacin-Aα, -Aγ, -Dα and -Dγ.

Another object of the present invention is to provide an aculeacin group of antibiotics active against pathogenic fungi and yeasts.

Figure 2:
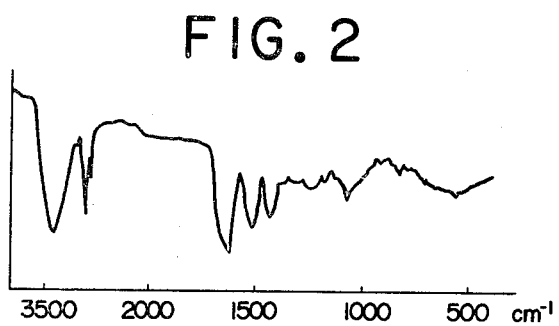
Figure 4:
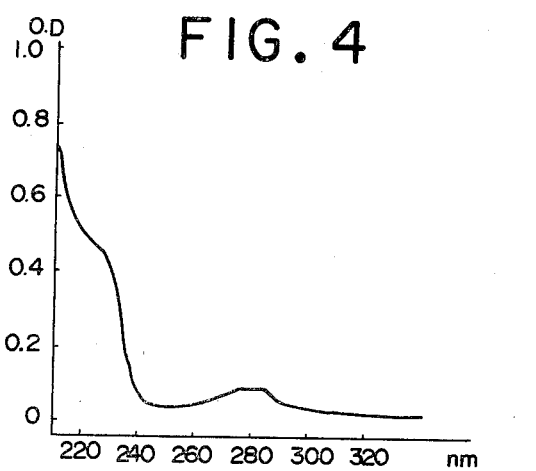
Figure 5:
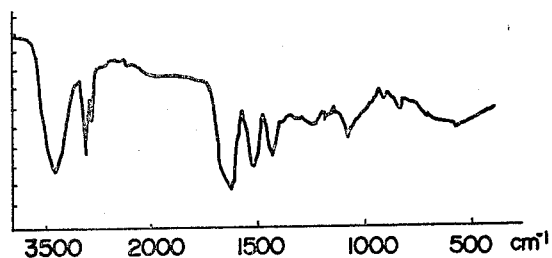
Figure 7:
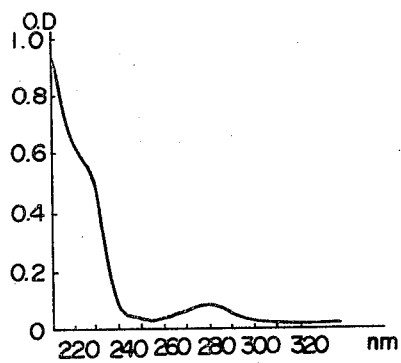
Figure 8:
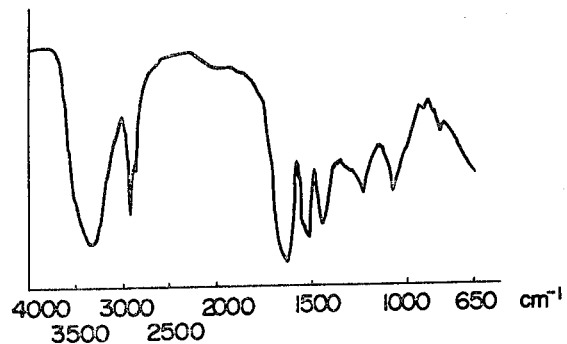
Figure 9:
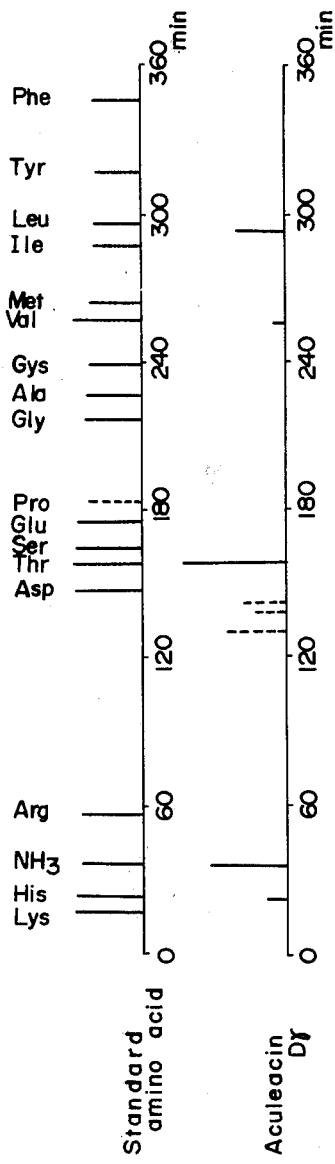
Figure 12:
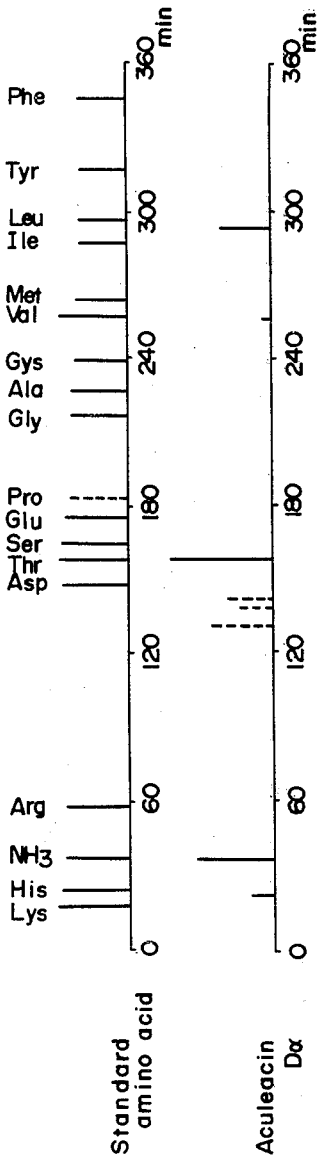
Figure 10:
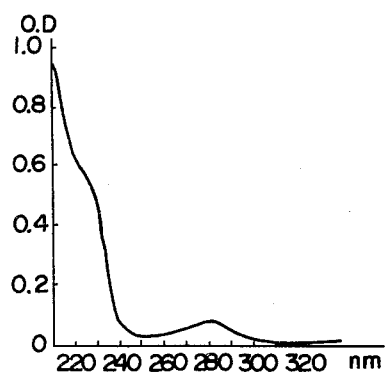
Figure 11:
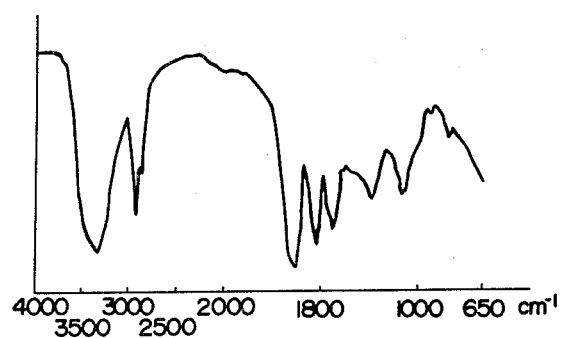

These and other objects, features and advantages of the present invention will become more apparent to any person skilled in the art upon reading the more detailed description set forth hereinbelow, in connection with the accompanying drawings, which show the following:

FIG. 1—ultraviolet absorption spectrum of aculeacin-Aα in methanol;
FIG. 2—infrared absorption spectrum of aculeacin-Aα;
FIG. 3—amino acid analysis of aculeacin-Aα;
FIG. 4—ultraviolet absorption spectrum of aculeacin-Aγ in methanol;
FIG. 5—infrared absorption spectrum of aculeacin-Aγ;
FIG. 6—amino acid analysis of aculeacin-Aγ;
FIG. 7—ultraviolet absorption spectrum of aculeacin-Dγ in methanol;
FIG. 8—infrared absorption spectrum of aculeacin-Dγ;
FIG. 9—amino acid analysis of aculeacin-Dγ;
FIG. 10—ultraviolet absorption spectrum of aculeacin-Dα in methanol;
FIG. 11—infrared absorption spectrum of aculeacin-Dα; and
FIG. 12—amino acid analysis of aculeacin-Dα.

Aculeacin group antibiotics consist of aculeacin-Aα, -Aγ, -Dα and -Dγ which are produced by culturing *Aspergillus aculeatus* M 4845 NRRL 11270, having strong anti-fugal activity, showing the peak of ultraviolet absorption at 278 nm and containing threonine as amino acid component. Since the aculeacin group of antibiotics are peptide antibiotics, hereinafter these groups of antibiotics will be designated as aculeacins.

According to this invention, aculeacins are produced by inoculating a strain of *Aspergillus aculeatus* M 4845 NRRL 11270 in a suitable nutrient medium. The cultivation of the microorganism can be carried out in a number of different ways such as liquid culture or solid culture. In an industrial production, submerged aeration culture inoculated with a 1–2 days cultured broth or spore suspension of *Aspergillus aculeatus* M 4845 NRRL 11270 is preferable.

Nutrient media which are useful for the production of aculeacins may include an assimilable source of carbon such as glucose, sucrose, lactose, maltose, starch, dextran, molasses and glycerol; an assimilable source of organic and inorganic nitrogen such as corn steep liquor, soybean powder, cotton seed oil, wheat gluten, meat extract, yeast extract, yeast, casein hydrolyzate, peptone and ammonium salt or nitrate, and the media further include salts such as phosphate, magnesium, calcium, potassium, sodium, zinc, ferric iron or manganese.

The culturing temperature for production of aculeacins may be selected within the range of temperature in which the microorganism can grow and aculeacins can be produced, and is preferably 25°–28° C.

The culturing period is generally 70–90 hours, and when the culture broth reaches maximum potency in terms of antibiotic production, the cultivation should of course be terminated.

In cultured broth obtained thus, aculeacins are accumulated in mycelia and partially in the outside of mycelia.

Aculeacins can be assayed by cup-assay method or paper disc-assay method using *Candida albicans* or *Trichophyton asteroides* as test organisms.

Aculeacins can be preferably and effectively isolated from mycelia.

According to a preferred procedure, the whole broth is filtered to obtain mycelia containing aculeacins using a drum-filter, filter-press or centrifugal separator. The thus-obtained wet mycelia is extracted with water:miscible organic solvent such as alcohol and acetone, then solvent in the extract is distilled off, the residue is diluted with water, further the diluent is extracted with n-butanol or ethyl acetate and the extract is washed with water and concentrated under reduced pressure to obtain oily material. The oily material can be purified by adsorption or partition chromatography using active alumina, silica gel or the like, and the thus-obtained active fraction is concentrated to obtain the powder showing single spot on thin layer chromatography by several developing solvent systems.

The physico-chemical properties of aculeacins are as follows:

1. Elementary analysis:

|  | C% | H% | N% |
|---|---|---|---|
| Aculeacin-Aα | 56.48 | 8.60 | 9.24 |
| Aculeacin-Aγ | 54.70 | 8.23 | 10.51 |
| Aculeacin-Dα | 55.96 | 8.44 | 9.96 |
| Aculeacin-Dγ | 57.55 | 8.32 | 8.94 |

Sulfur and halogen are not detected.

2. Molecular weight:

|  | Rast Method | Amino Acid Analysis* | Gel-filtration Method**** |
|---|---|---|---|
| Aculeacin-Aα | 1015 | (860)n** | 800 ± 110 |
| Aculeacin-Aγ | 1021 | (860)n** | 800 ± 110 |
| Aculeacin-Dα | 1243 | (555)n*** | 850 ± 100 |
| Aculeacin-Dγ | 1265 | (555)n*** | 850 ± 100 |

*Calculated from detected amount of threonine.
**3.0 μ Mol of threonine were detected from hydrolyzate of 2.6 mg. of aculeacin-Aα or -Aγ.
***4.8 μ Mol of threonine was detected from hydrolyzate of 2.6 mg. of aculeacin-Dα or -Dγ.
****Estimated by elution time in comparison with known molecular weight antibiotics using Sephadex LH-20 [Pharmacia Fine Chemicals Co., Sweden ].

3. Melting point:
Aculeacin-Aα: 174°–177° C.
Aculeacin-Aγ: 172°–175° C.
Aculeacin-Dα: 159°–162° C.
Aculeacin-Dγ: 159°–162° C.

4. Specific rotation: $[\alpha]_D^{23}$ (c=0.25 methanol)
Aculeacin-Aα: −46.8°
Aculeacin-Aγ: −47.4°
Aculeacin-Dα: −45.7°
Aculeacin-Dγ: −46.7°

5. Color reaction:
Showing in the following table:

| Color Reaction + = positive − = negative | Aculeacins | | | |
|---|---|---|---|---|
|  | Aα | Aγ | Dα | Dγ |
| Pauli reaction | + | + | + | + |
| Folin reaction | + | + | + | + |
| HIO₄-benzidine reaction | + | + | + | + |
| KMnO₄ decolorization reaction | + | + | + | + |
| Molisch reaction | ± | ± | ± | ± |
| Biuret reaction | ± | ± | ± | ± |
| Xanthoprotein reaction | ± | ± | ± | ± |
| Tollens reaction | ± | ± | ± | ± |
| Ninhydrin reaction | − | − | − | − |
| Benedict reaction | − | − | − | − |
| Sakaguchi reaction | − | − | − | − |
| Ehrlich reaction | − | − | − | − |
| Ferric chloride reaction | − | − | − | − |
| Dragendorff's reaction | − | − | − | − |
| 2,4-dinitrophenylhydrazine reaction | − | − | − | − |

6. Solubility:
Soluble: lower alcohols.
Slightly soluble: ethyl acetate.
Almost insoluble: acetone, chloroform, n-hexane, petroleum ether and water.

7. Aculeacins are impossible to titrate due to decomposition at an alkaline pH, and due to slight solubility aculeacins are immobile upon electrophoresis. Aculeacins cannot be transferred from butanol solution to water at pH 2–9. This may indicate the neutral nature of aculeacins.

8. Color: White crystalline powder.

9. Stability:
Stable at 37° C. for 20 hours at acidic and neutral condition.
Unstable at alkaline condition.

10. Ultraviolet absorption spectrum:
FIG. 1: Aculeacin-Aα in methanol (32.4 γ/ml).
FIG. 4: Aculeacin-Aγ in methanol (32.4 γ/ml).
FIG. 7: Aculeacin-Dγ in methanol (40 γ/ml).
FIG. 10: Aculeacin-Dα in methanol (40 γ/ml).

As shown in the figures aculeacin-Aα and -Aγ have maximum peak at 278 nm and shoulders at 226 and 283 nm, and aculeacin-Dα and -Dγ have the maximum peak at 278 nm and shoulders at 226 nm and 284 nm.

$E_{1\ cm}^{1\%}$ of each compound are shown in the following table:

| | In Methanol | | | |
|---|---|---|---|---|
| | 226 nm (shoulder) | 278 nm (peak) | 283 nm (shoulder) | 284 nm (shoulder) |
| Aα | 146 | 16.0 | 13.5 | — |
| Aγ | 145 | 15.5 | 13 | — |
| Dα | 138 | 17.5 | — | 14.7 |
| Dγ | 137 | 17.0 | — | 14.2 |

11. Infrared absorption spectrum (KBr tablet):

| Aculeacins | Absorption bands (cm$^{-1}$) | | | | | |
|---|---|---|---|---|---|---|
| Fig. 2: Aculeacin-Aα | 3350, | 2910, | 2840, | 1620, | 1510, | 1435. |
| Fig. 5: Aculeacin-Aγ | " | " | " | " | " | " |
| Fig. 8: Aculeacin-Dγ | " | " | " | " | " | " |
| Fig. 11: Aculeacin-Dα | " | " | " | " | " | " |

12. Rf value:
Carrier: silica gel sheet (product of Eastman Kodak Co., Eastment Chromagram Sheet No. 6060).
Solvent:
A: chloroform-methanol (10:3);
B. ethyl acetate-methanol-water (20:4:1);
C: ethyl acetate-n-butanol (3:1) saturated with water.
Developer: iodine.
Bioassay using *Candida albicans*.

| Solvent System | A | B | C |
|---|---|---|---|
| Aculeacin-Aα | 0.47 | 0.28 | 0.37 |
| Aculeacin-Aγ | 0.47 | 0.28 | 0.37 |
| Aculeacin-Dα | 0.67 | 0.35 | 0.42 |
| Aculeacin-Dγ | 0.67 | 0.35 | 0.42 |

13. Retention time on liquid chromatography:

| | Retention time (minutes) |
|---|---|
| Aculeacin-Aα | 7.9 |
| Aculeacin-Aγ | 12.3 |
| Aculeacin-Dα | 9.2 |
| Aculeacin-Dγ | 14.1 |

5 mg/ml of aculeacins dissolved in 8 μl. of methanol, are charged on a column 5×500 mm; carrier polystyrene resin; developer: 85% aqueous methanol containing 0.01% triethylamine; column temperature: 55° C.; type: Hitachi 634, product of Hitachi Corp., Japan.

14. Hydrolysis:

| | Hydrolyzate |
|---|---|
| Aculeacin-Aα | myristic acid |
| Aculeacin-Aγ | palmitic acid |
| Aculeacin-Dα | myristic acid |
| Aculeacin-Dγ | palmitic acid |

Aculeacins are hydrolyzed by 6 N-HCl at 110° C. and extracted with ether. Ether layer was charged on a gas chromatogram and free fatty acid was qualitatively analyzed.

15. Amino acid composition:
Aculeacins are hydrolyzed with 6 N HCl, at 110° C. for 20 hours and ninhydrine positive components are analyzed by automatic amino acids analyzer (Japan Electron Optical Corp., Type: JLC-5AH analyzer). Results are shown in FIG. 3 (aculeacin-Aα), FIG. 6 (aculeacin-Aγ), FIG. 9 (aculeacin-Dγ) and FIG. 12 (aculeacin-Dα) in which threonine and several unknown ninhydrin-positive components are found.

Aculeacins are peptide antibiotics almost insoluble in water in accordance with the physico-chemical properties hereinabove.

Among the antibiotics hitherto reported, having ultraviolet absorption maxima at 278 nm in methanol, which resemble aculeacin-Aα, -Aγ, -Dα and -Dγ respectively, are myroridin (Japan. Pat. Publ. No. 45-12275), athlestatin (Japan. Pat. Publ. No. 41-12668, monilin (Takeda Institute Annual Report, 14, 8–10 [1955]), oryazamycin (Japan. Pat. Publ. 38-2800), saramycetin (Antimicrobial Agents and Chemotherapy, 1961, 436–666), unamycin (J. Antibiotics, Ser. A, 13, 114–120 [1960]), vengicide (British Pat. No. 764,198), aculeacin-A and aculeacin-D (U.S. Pat. No. 3,978,210) and Echinocandin B (antibiotic A32204, Swiss Pat. No. 568,386). Aculeacins are however different from those antibiotics for the following reasons:

Myroridin is a basic water-soluble antibiotic which differs from aculeacins. Athlestatin is similar to aculeacins in its physico-chemical properties and biological properties; however, the specific rotation of athlestatin $[\alpha]_D^{20} = -64°$ (c=0.5 methanol) and ultraviolet absorption maxima of athlestatin are at 278 and 225 nm, and its elemental analysis is C: 55.25%, H: 7.50% and N: 9.41%, which is different from aculeacins. Monilin is a basic nucleoside substance and the nitrogen content in its elemental analysis is higher than that of aculeacins. Oryzamycin is an acidic oily substance. Saramycetin yields aspartic acid, cystine, glycine and threonine upon hydrolysis, and unamycin is an acidic polyene substance. Vengicide is similar to monilin, a nucleoside substance. Aculeacin-A, aculeacin-D and Echinocandin B are similar to aculeacin-Aα -Aγ, and aculeacin-Dα and -Dγ, respectively in their physico-chemical properties and biological properties; however, aculeacins of the present invention are different from the known aculeacin-A, -D and Echinocandin B in their retention times on liquid chromatography in which aculeacin-Aα is 7.9 min.; aculeacin-Aγ is 12.3 min., and hydrolyzates, namely, myristic acid from aculeacin-Aα and -Dα, palmitic acid from aculeacin-Aγ and -Dγ and linoleic acid and stearic acid from Echinocandin B.

Thus, aculeacin-Aα, -Aγ, -Dα and -Dγ are novel antibiotics different from the antibiotics hitherto known in this art.

The biological properties of the aculeacins are as follows:

| 80% Growth Inhibitory Concentration (γ/ml) | | | | |
|---|---|---|---|---|
| | Aculeacin-Aα | -Aγ | -Dα | -Dγ |
| *Trichophyton asteroides* | 0.004 | 0.004 | 0.001 | 0.002 |
| *Trichophyton rubrum* | 0.006 | 0.006 | 0.002 | 0.003 |
| *Microsporum gypseum* | 0.008 | 0.008 | 0.002 | 0.004 |
| *Fusarium oxysporum* f. lini | 2.0 | 2.0 | 0.1 | 1.0 |
| *Diaporthe phaseolorum* | 0.01 | 0.01 | 0.0025 | 0.005 |
| *Ascochyta soyaecola* | 0.08 | 0.08 | 0.02 | 0.04 |
| *Sclerotium bataticola* | 0.08 | 0.08 | 0.02 | 0.02 |
| *Glomerella cingulata* | 0.06 | 0.03 | 0.01 | 0.03 |
| *Helminthosporium oryzae* | 0.008 | 0.008 | 0.002 | 0.004 |

Acute toxicity on mouse:
$LD_{50}$ of aculeacin injections prepared by using sodium deoxycholate additives is as follows:

| Route of | LD₅₀ (mg/kg) | | | |
|---|---|---|---|---|
| Administration | Aα | Aγ | Dα | Dγ |
| i.v. | 350 | 350 | >1000 | >1000 |
| i.m. | 600 | 600 | >1000 | >1000 |

The following examples are only for illustration of the process and products of the present invention and are not to be construed as limiting.

EXAMPLE 1

One hundred milliliters of aqueous medium consisting of glucose 2%, polypeptone 1%, corn steep liquor 1%, $KH_2PO_4$ 0.2% and $MgSO_4.7H_2O$ 0.1% was introduced into 500 ml. Erlenmeyer flasks (pH 6.5), sterilized at 120° C. for 15 mins. *Aspergillus aculeatus M* 4845 NRRL 11270 is inoculated therein and shake cultured at 26° C. for 48 hours. The cultured broth was aseptically inoculated into 15 l. of aqueous medium (pH 6.5) consisting of saccharose 1.5%, dextrin 1.4%, polypeptone 2%, corn steep liquor 0.45%, $KH_2PO_4$ 0.2%, $MgSO_4$ 0.1% and antifoamer (Trade Name BC-51Y, product of Nippon Yushi Co.) in a 30 l. capacity jar fermenter, and fermented at 26° C. for 96 hours with aeration of 30 l./min. and agitation of 250 r.p.m. to obtain about 15 l. of fermented broth. The broth assayed aculeacin activity in filtrate and in mycelia.

EXAMPLE 2

Cultured broth (10 l.) obtained in Example 1 is filtered by suction to obtain wet mycelia (1 kg). To the wet mycelia was added 5 l. of methanol, the mixture extracted under stirring for 2 hours, and methanol solution was obtained by vacuum filtration. Residual mycelia were again extracted with methanol (5 l.) to obtain extract. Both extracts were combined, and the methanol was distilled off under reduced pressure to obtain 2 l. of concentrate. Thereto was added 2 l. of water and the medium was extracted twice with 2 l. of n-butanol each time. The n-butanol layer was collected. After the n-butanol layer was washed with water (5 l.), the butanol was concentrated in vacuo while adding a small amount of water to obtain a dark brown colored viscous concentrate. Thereto was added n-hexane (500 ml) to precipitate the material which was washed with ethyl acetate to obtain 12.5 g. of crude aculeacins.

EXAMPLE 3

12.5 g. of crude aculeacins obtained in Example 2 dissolved in a small amount of methanol was adsorbed on silica gel (25 g., produce of E. Merck AG), thereafter methanol was distilled off under reduced pressure. The thus-obtained silica gel was placed on a column (inside diameter 50 mm.) packed with silica gel (600 g.) and eluted with a mixed solvent of ethyl acetate-isopropanol-water (10:1.5:0.7) to fractionate each 45 ml. in one fraction.

EXAMPLE 4

The fractions Nos. 43–57 obtained in Example 3 were combined and dried in vacuo. 10 µl. of the dried material dissolved in methanol was charged on high pressure liquid chromatography (Type: Hitachi 634, produce of Hitachi Corp., column: 5×500 mm., carrier: polystyrene, developer: 85% aqueous methanol containing 0.01% triethylamine, column temperature: 55° C.) and the fractions having retention time values of 7.4–8.4 min. were collected. The fractions obtained by repeated operation were combined and dried in vacuo, then dissolved in a small amount of methanol. Thereto was added a mixed solvent of ethyl acetate-n-hexane (1:1). Precipitate was collected to obtain 230 mg. of purified aculeacin-Aα.

EXAMPLE 5

Example 4 was repeated, except that now the fractions having retention time values of 11.4–13.4 min. were collected and the remaining treatment was performed in the same way as in Example 4 to obtain 50 mg. of purified aculeacin-Aγ.

EXAMPLE 6

The fractions Nos. 32–42 obtained in Example 3 were combined and dried in vacuo to obtain a white powder (900 mg.), then dissolved in a small amount of methanol. The methanol solution was adsorbed on silica gel (2 g.); thereafter methanol was distilled off under reduced pressure. The thus-obtained silica gel was placed on a column (inside diameter 25 mm.) packed with silica gel (45 g., product of Tokoyo Kasei Co.) and eluted with a mixed solvent of chloroform-methanol (10:1.5). Fractions Nos. 76–141 (5 g. per fraction) were collected and the combined fractions were dried to obtain 370 mg. of the material containing aculeacin-Dα and -Dγ. 10 µl. of the methanol solution thereof were charged on the same condition of high pressure liquid chromatography as in Example 4 and the fractions having retention time values of 8.6–9.8 min. were collected. The fractions obtained by repeated operation were combined and dried in vacuo, then dissolved in a small amount of methanol. Thereto was added a mixed solvent of ethyl acetate-n-hexane (1:1). Precipitate was collected to obtain 115 mg. of purified aculeacin-Dα.

EXAMPLE 7

Example 6 was repeated except that the fractions having retention time values of 14.4–16.4 min. were collected and the remaining treatment was performed in the same way as in Example 6 to obtain 15 mg. of purified aculeacin-Dγ.

What we claim is:

1. An antifungal antibiotic aculeacin selected from the group consisting of aculeacin-Aα, aculeacin-Aγ, aculeacin-Dα and aculeacin-Dγ, said aculeacins having substantially the following physico-chemical properties:

Elementary analysis:

|  | C% | H% | N% |
|---|---|---|---|
| Aculeacin-Aα | 56.48 | 8.60 | 9.24 |
| Aculeacin-Aγ | 54.70 | 8.23 | 10.51 |
| Aculeacin-Dα | 55.96 | 8.44 | 9.96 |
| Aculeacin-Dγ | 57.55 | 8.32 | 8.94 |

Sulfur and halogen are not detected.

Molecular weight:

|  | Rast Method | Amino Acid Analysis* | Gel-filtration Method |
|---|---|---|---|
| Aculeacin-Aα | 1015 | (860)n | 800 ± 110 |
| Aculeacin-Aγ | 1021 | (860)n | 800 ± 110 |
| Aculeacin-Dα | 1243 | (555)n | 850 ± 100 |
| Aculeacin-Dγ | 1265 | (555)n | 850 ± 100 |

*Calculated from detected amount of threonine

Melting point:
Aculeacin-A$\alpha$: 174°–177° C.
Aculeacin-A$\gamma$: 172°–175° C.
Aculeacin-D$\alpha$: 159°–162° C.
Aculeacin-D$\gamma$: 159°–162° C.

Specific rotation: $[\alpha]_D^{23}$ (c-0.25 methanol)
Aculeacin-A$\alpha$: −46.8°
Aculeacin-A$\gamma$: −47.4°
Aculeacin-D$\alpha$: −45.7°
Aculeacin-D$\gamma$: −46.7°

Ultraviolet absorption spectrum:
Aculeacin-A$\alpha$ in methanol (32.4 $\gamma$/ml) as shown in FIG. 1 in the accompanying drawings
Aculeacin-A$\gamma$ in methanol (32.4 $\gamma$/ml) as shown in FIG. 4 in the accompanying drawings
Aculeacin-D$\gamma$ in methanol (40 $\gamma$/ml) as shown in FIG. 7 in the accompanying drawings
Aculeacin-D$\alpha$ in methanol (40 $\gamma$/ml) as shown in FIG. 10 in the accompanying drawings.

2. A compound as claimed in claim 1, in which said aculeacin is said aculeacin-A$\alpha$.

3. A compound as claimed in claim 1, in which said aculeacin is said aculeacin-A$\gamma$.

4. A compound as claimed in claim 1, in which said aculeacin is said aculeacin-D$\alpha$.

5. A compound as claimed in claim 1, in which said aculeacin is said aculeacin-D$\gamma$.

6. A process for the production of an antifungal antibiotic aculeacin selected from the group consisting of aculeacin-A$\alpha$, aculeacin-A$\gamma$, aculeacin-D$\alpha$ and aculeacin-D$\gamma$, comprising culturing the microorganism *Aspergillus aculeatus* NRRL 11270 in a nutrient medium containing assimilable carbon and nitrogen sources, and isolating a said aculeacin therefrom.

* * * * *